(12) United States Patent
Baguley et al.

(10) Patent No.: US 7,585,893 B2
(45) Date of Patent: Sep. 8, 2009

US007585893B2

(54) ANTI-CANCER COMPOSITION COMPRISING DMXAA OR RELATED COMPOUND

(75) Inventors: Bruce Charles Baguley, Auckland (NZ); Lai-Ming Ching, West Harbour (NZ); Philip Kestell, Auckland (NZ); Liangli Zhao, Mt. Roskill (NZ)

(73) Assignee: Cancer Research Technology Limited (GB)

( * ) Notice: Subject to any disclaimer, the term of this patent is extended or adjusted under 35 U.S.C. 154(b) by 134 days.

(21) Appl. No.: 11/116,798

(22) Filed: Apr. 28, 2005

(65) Prior Publication Data

US 2006/0009505 A1    Jan. 12, 2006

Related U.S. Application Data

(63) Continuation of application No. PCT/GB03/04688, filed on Oct. 30, 2003.

(30) Foreign Application Priority Data

Nov. 1, 2002    (GB) ................... 0225508.1

(51) Int. Cl.
    *A61K 31/35*    (2006.01)
(52) U.S. Cl. .................. 514/457; 514/449; 514/455
(58) Field of Classification Search ................ 514/457, 514/449, 455
    See application file for complete search history.

(56) References Cited

U.S. PATENT DOCUMENTS

| | | | |
|---|---|---|---|
| 3,678,077 A | 7/1972 | Nakanishi et al. | |
| 4,602,034 A | 7/1986 | Briet et al. | |
| 4,704,355 A | 11/1987 | Bernstein et al. | |
| 5,126,129 A * | 6/1992 | Wiltrout et al. | 424/85.2 |
| 5,281,620 A | 1/1994 | Denny et al. | |
| 5,464,826 A | 11/1995 | Grindey et al. | |
| 5,620,875 A | 4/1997 | Hoffman et al. | |
| 5,817,684 A | 10/1998 | Fleisch et al. | |
| 5,863,904 A | 1/1999 | Nabel et al. | |
| 5,910,505 A | 6/1999 | Fleisch et al. | |
| 6,174,873 B1 * | 1/2001 | Wrenn, Jr. | 514/45 |
| 6,194,454 B1 * | 2/2001 | Dow | 514/522 |
| 6,667,337 B2 | 12/2003 | Wilson | |
| 6,806,257 B1 | 10/2004 | Lee et al. | |
| 2001/0041713 A1 | 11/2001 | Waldstreicher et al. | |
| 2003/0003092 A1 | 1/2003 | Krissansen et al. | |
| 2004/0087611 A1 | 5/2004 | Baguley et al. | |
| 2004/0204480 A1 | 10/2004 | Wilson et al. | |
| 2005/0131059 A1 | 6/2005 | Wang et al. | |
| 2007/0060637 A1 | 3/2007 | Wilson et al. | |
| 2007/0082937 A1 | 4/2007 | Baguley et al. | |
| 2008/0070847 A1 | 3/2008 | Wilson et al. | |
| 2008/0070848 A1 | 3/2008 | Wilson et al. | |
| 2008/0070849 A1 | 3/2008 | Wilson et al. | |
| 2008/0070886 A1 | 3/2008 | Wilson et al. | |

FOREIGN PATENT DOCUMENTS

| | | |
|---|---|---|
| DE | 2015265 A1 | 10/1970 |
| DE | 19721211 A1 | 11/1998 |
| EP | 0278176 A | 8/1988 |
| EP | 0326149 A2 | 8/1989 |
| EP | 0385467 A1 | 9/1990 |
| EP | 0488718 A2 | 6/1992 |
| EP | 0551200 A1 | 7/1993 |
| EP | 0743064 | 11/1996 |
| EP | 0584001 B1 | 5/1997 |
| GB | 0121285.1 | 9/2001 |
| GB | 0206839.3 | 5/2002 |
| GB | 0225508.1 | 11/2002 |
| GB | 0604114.9 | 3/2006 |
| GB | 0517386.9 | 8/2006 |
| GB | 0517387.7 | 8/2006 |
| JP | 09040690 A2 | 2/1997 |
| JP | 2001247459 | 9/2001 |
| NZ | 336259 | 6/1999 |
| NZ | 506060 | 7/2000 |
| WO | WO 91/04014 | 4/1991 |
| WO | WO 94/23753 A1 | 10/1994 |
| WO | WO 95/09621 A1 | 4/1995 |
| WO | WO 96/32418 A1 | 10/1996 |
| WO | WO 96/36347 A1 | 11/1996 |
| WO | WO 97/04761 A1 | 2/1997 |
| WO | WO 97/34482 A1 | 9/1997 |
| WO | WO 98/25600 A1 | 6/1998 |
| WO | WO 98/25615 A1 | 6/1998 |
| WO | WO 98/25616 A1 | 6/1998 |

(Continued)

OTHER PUBLICATIONS ptcl.chem.ox.ac.uk/MSDS, Jun. 27, 2003, 1 page.*
Cecil Text book of Medicine, 20th Edition vol. 1 W. B. Saunders Company, 1997, pp. 1004-1010.*
Philpott et al. Cancer Chemother. Pharmacol. (1995) 36:143-148.*
Wilkinson et al. Cancer Chemotherapy Pharmacol, 1982;10:33-35.*
L. Zhao, et al., Oral activity and pharmacokinetics of 5, 6-dimethylxanthenone-4-acetic acid (DMXAA) in Mice, *Cancer Chemother. Pharmacol.*, 2002, 49: 20-26, published online Nov. 10, 2001.
Zhao, L., et al., Improvement of the Antitumor Activity of Intraperitoneally and Orally Administered 5,6-Dimethylxanthenone-4-Acetic Acid by Optimal Scheduling, Clinical Cancer Research, vol. 9, Dec. 15, 2003, pp. 6545-6550.

(Continued)

*Primary Examiner*—Michael G Hartley
*Assistant Examiner*—Shirley V Gembeh
(74) *Attorney, Agent, or Firm*—Foley & Lardner LLP (57) ABSTRACT

The present invention relates to the use of compounds such as compounds of the xanthenone acetic acid class such as 5,6-dimethylxanthenone-4-acetic acid (DMXAA) for the treatment of cancer, wherein the compounds are administered gastrointestinally, preferably orally. More particularly, the invention is concerned with the use of such compounds, wherein the compound is delivered to the site of action in the patient to be treated in two or more doses.

9 Claims, 2 Drawing Sheets

FOREIGN PATENT DOCUMENTS

| | | |
|---|---|---|
| WO | WO 98/42332 A1 | 10/1998 |
| WO | WO 98/42334 A1 | 10/1998 |
| WO | WO 98/42335 A1 | 10/1998 |
| WO | WO 98/42336 A1 | 10/1998 |
| WO | WO 98/42337 A1 | 10/1998 |
| WO | WO 98/42345 A1 | 10/1998 |
| WO | WO 98/42346 A1 | 10/1998 |
| WO | WO 98/42650 A2 | 10/1998 |
| WO | WO 00/10600 A3 | 3/2000 |
| WO | WO 00/16798 A1 | 3/2000 |
| WO | WO 00/48591 A1 | 8/2000 |
| WO | WO 00/76497AI | 12/2000 |
| WO | WO 01/34135 A2 | 5/2001 |
| WO | WO 01/34137 A2 | 5/2001 |
| WO | WO 01/34197 A2 | 5/2001 |
| WO | WO 01/34198 A2 | 5/2001 |
| WO | WO 02/09700 A1 | 2/2002 |
| WO | WO 03/020259 A2 | 3/2003 |
| WO | WO 03/080044 | 10/2003 |
| WO | WO 2005/027974 A1 | 3/2005 |
| WO | WO 2007/023302 | 3/2007 |
| WO | WO 2007/023307 | 3/2007 |

OTHER PUBLICATIONS

U.S. Appl. No. 12/064,632, filed Aug. 28, 2006, Green, et al.
U.S. Appl. No. 12/064,633, filed Aug. 25, 2006, Green, et al.
Aitken, et al.; "Synthesis and Antitumour Activity of New Derivatives of Flavone-8-acetic Acid (FAA), Part 4: Variation of the Basic Structure"; Arch. Pharm. Pharm. Med. Chem. (2000), 333(6):181-188.
Arbuck, et al.; "An Overview of Topoisomerase I-Targeting Agents"; Semin. Hematol. 1998, 35(3 supp. 4):3-12.
Atwell, et al.; "Potential Antitumor Agents. 60. Relationships between Structure and in Vivo Colon 38 Activity for 5-Substituted 9-Oxoxanthene-4-acetic Acids"; J. Med. Chem. (1990), 33:1375-1379.
Atwell, et al.; "Synthesis and anti-tumor activity of topologically-related analogues of flavoneacetic acid"; Anti-Cancer Drug Design (1989), 4(2):161-169.
Avastin. Http://www.centerwatch.com/patient/drugs/dru851.html, Jun. 29, 2004.
Baguley, et al.; "Immunomodulatory Actions of Xanthenone Anticancer Agents"; BioDrugs; (1997), 8(2):119-127.
Baguley, et al.; "Mechanisms of Tumor Blood Flow Inhibition by The Antitumour Drug DMXAA (5,6-dimethylxanthenone-4-acetic acid"; Proceedings of the 11th NCI EORTC AACR Symposium; Copyright © 2000 Stichting NCI-EORTC Symposium on new drugs in cancer therapy; publ. By the AACR; Published as a Supplement to Clinical Cancer Research, vol. 6, Nov. 2000.
Baguley, et al.; Poster Abstract 138, of abstracts book for the 16th EORTC-NCI-AACR 2004 meeting on "Molecular Targets and Cancer Therapeutics"; Geneva, Switzerland (Sep. 28 to Oct. 1, 2004).
Baguley, et al.; "Potential of DMXAA combination therapy for solid tumors"; Expert Rev. Anticancer Ther. (2002), 2(5):593-603.
Baguley, et al.; "Serotonin involvement in the antitumour and host effects of flavone-8-acetic acid and 5,6-dimethylxanthenone-4-acetic acid"; Cancer Chemother. Pharmacol (1993), 33(1):77-81.
Baguley, et al.; "Evidence that the 5-hydroxytryptamine antagonist, cyproheptadine, modulates nitric oxide production in mice in response to flavone acetic acid, vinblastine and other agents"; Biol. Nitric Oxide, Proc. Int. Meet.; Meeting Date 1991, vol. 2, (1992); 222-224.
Baguley, et al.; "Increased Plasma Serotonin Following Treatment With Flavone-8-Acetic Acid, 5,6-Dimethylxanthenone-4-Acetic Acid, Vinblastine, and Colchicine: Relation to Vascular Effects"; Oncology Research; (1997) 9(2), 55-60.
Barefoot, R.; "Speciation of platinum compounds: a review of recent applications in studies of platinum anticancer drugs"; Journal of Chromatography B (2001), 751:205-211.

Begley, et al.; "The Blood-Brain-Barrier: Principles for Targeting Peptides and Drugs to the Central Nervous System"; J. Pharm. Pharmacol. (1996), 48:136-146.
Bibby, et al.; "Flavone acetic acid—from laboratory to clinic and back"; Anti-Cancer Drugs (1993), 4:3-17.
Bibby, et al.; "Reduction of Tumor Blood Flow by Flavone Acetic Acid: A Possible Component of Therapy"; J. Natl. Cancer Inst. (1989), 81:216-220.
Brem, et al.; "Interstitial chemotherapy with drug polymer implants for the treatment of recurring gliomas"; J. Neurosurg. (1991), 74:441-446.
Browne, et al.; "Suppression of serum tumour necrosis factor-alpha by thalidomide does not lead to reversal of tumour vascular collapse and anti-tumour activity of 5, 6-dimethylxanthenone-4-acetic acid"; Anticancer Res. (1998), 18(6A):4409-4414.
Calabresi, et al.; "The Pharmacological Basis of Therapeutics, Ninth Edition," (1996), Goodman & Gilman's The Pharmacological Basis of Therapeutics. Section X, Chemotherapy of Neoplastic Diseases, pp. 1225-1229.
Cao, et al.; "Interferon-inducible Protein 10 Induction and Inhibition of Angiogenesis in Vivo by the Antitumor Agent 5, 6-Dimethylxanthenone-4-acetic Acid (DMXAA)"; Cancer Research (2001), 61(4):1517-1521.
Cao, et al.; "Thalidomide increases both intra-tumoural tumour necrosis factor-alpha production and anti-tumour activity in response to 5, 6-dimethylxanthenone-4-acetic acid"; Br. J. Cancer (1999), 80(5/6):716-723.
Chaplin, et al.; "Antivascular approaches to solid tumor therapy; evaluation of tubulin binding agents"; Proc. Annu. Meet. Am. Assoc. Cancer Res., Mar. 1996, vol. 37, #3009: 440-441 and Abstract.
Ching, et al.; "Antitumour responses to flavone-8-acetic acid and 5, 6-dimethylxanthenone-4-acetic acid in immune deficient mice"; Br. J. Cancer (1992), 66(1):128-130.
Ching, et al.; "Effect of Tumor Growth on the Macrophage Response to the Antitumour Agent 5,6-Dimethylxanthenone-4-acetic Acid"; Anticancer Research (1993), 13(6A):2069-2076.
Ching, et al.; "Haematological effects in mice of the antitumour agents xanthenone-4-acetic acid, 5, 6-dimethylxanthenone-4-acetic acid and flavoneacetic acid"; Cancer Chemother. Pharmacol. (1991), 28(6):414-419.
Ching, et al.; "In vitro Methods for Screening Agents with an Indirect Mechanism of Antitumour Activity: Xanthenone Analogues of Flavone Acetic Acid"; Eur. J. Cancer (1991), 27(12):1684-1689.
Ching, et al.; "Induction of Natural Killer Activity by Xanthenone Analogues of Flavone Acetic Acid: Relation with Antitumour Activity"; Eur. J. Cancer (1991), 27(1):79-83.
Ching, et al.; "Induction of STAT and NF-kappa-B Activation by the Antitumor Agents 5,6-Dimethylxanthenone-4-acetic Acid and Flavone Acetic Acid in a Murine Macrophage Cell Line"; Biochemical Pharmacology (1999), 58(7):1173-1181.
Ching, et al.; "Induction of Tumor Necrosis Factor-alpha Messenger RNA in Human and Murine Cells by the Flavone Acetic Acid Analogue 5, 6-Dimethylxanthenone-4-acetic acid"; Cancer Research (1994), 54(4):870-872.
Ching, et al.; "Stimulation of macrophage tumouricidal activity by 5, 6-dimethylxanthenone-4-acetic acid, a potent analogue of the antitumour agent flavone-8-acetic acid"; Biochemical Pharmacology (1992), 44(1):192-195.
Ching, et al.; "Effect of thalidomide on tumour necrosis factor production and anti-tumour activity induced by 5, 6-dimethylxanthenone-4-acetic acid"; Br. J. Cancer (1995), 72(2):339-343.
Ching, et al.; "Induction of intratumoral tumor necrosis factor (TNF) synthesis and hemorrhagic necrosis by 5, 6-dimethylxanthenone-4-acetic acid (DMXAA) in TNF knockout mice"; Cancer Res. (1999), 59(14):3304-3307.
Ching, et al.; "Interaction between endotoxin and the antitumour agent 5, 6-dimethylxanthenone-4-acetic acid in the induction of tumor necrosis factor and haemorrhagic necrosis of colon 38 tumors"; Cancer Chemother. Pharmacol. (1994), 35(2):153-160.
Ching, et al.; "Interaction of thalidomide, phthalimide analogues of thalidomide and pentoxifylline with the antitumour agent 5, 6-dimethylxanthenone-4-acetic acid: concomitant reduction of serum tumour necrosis factor-alpha and enhancement of antitumour activity"; Br. J. Cancer. (1998), 78(3):336-343.

Ching, et al.; "The Anti-Tumour and Immune-Modulatory Activites of Flavone Acetic and Xanthone Acetic Acids"; 1990; N.P. Das (ed.), flavanoids in Biology and Medicine III. Proceedings of the 3rd International Symposium on Flavonoids in Biology and Medicine; 381-391.

Cliffe, et al.; "Combining bioreductive drugs (SR 4233 or SN 23862) with the vasoactive agents flavone acetic acid or 5,6-dimethylxanthenone acetic acid"; Int. J. Radiation Oncology Biol. Phys. (1994), 29(2):373-377.

Coloma, et al.; "Transport across the primate Blood-Brain-Barrier of a genetically engineered Chimeric Monoclonal Antibody to the Human Insulin Receptor"; Pharmaceutical Research (2000), 17(3):266-274.

Combretastatin Update 1: "In Ohio Phase 1 Trial, Some Tumors Respond, Patients Experience Vascular Stress"; PSA Rising; Medical Pike Briefs; Headline Index: Clinical Trial Phase 1 Results; Nov. 8, 1999.

Corbett, et al.; "Activity of flavone acetic acid (NSC-347512) against solid tumors of mice"; Investigational New Drugs (1986), 4:207-220.

Djeha, et al.; "Synergistic in vivo antitumor activity in lung and colon cancer xenografts with the vascular disrupting agent DMXAA combined with bevacizumab"; Proc. Am. Assoc. Cancer. Res. Annual Meeting, (2006), 47:55.

Economou, et al.; "Tumour necrosis factor production by IL-2-activated macrophages in vitro and in vivo"; Immunology (1989), 67:514-519.

Everett, et al.; "Decarboxylation of the antitumour drugs flavone-8-acetic acid and xanthenone-4-acetic acid by nitrogen dioxide"; Anti-Cancer Drug Design (1994), 9(1):68-72.

Everett, et al.; "High-performance ion chromatography applied to free-radical mechanisms in drug design. The problem of ion analysis at high ionic strengths"; Journal of Chromatography A. (1997), 770(1/2):273-279.

Fujii, et al.; "Vaccination with B7-1 tumor and anti-adhesion therapy with RGD pseudo-peptide (FC-336) efficiently induce anti-metastatic effect"; Clinical & Experimental Metastasis (1998), 16:141-148.

Futami, et al.; "Cytokine induction and therapeutic synergy with interleukin-2 against murine renal and colon cancers by xanthenone-4-acetic acid derivatives"; J. Immunother. (1992), 12(4):247-255.

Galbraith, et al.; "Effects of 5,6-Dimethylxanthenone-4-acetic acid on Human Tumor Microcirculation Assessed by Dynamic Contrast-enhanced Magnetic Resonance Imaging"; J. Clinical Oncology (2002), 20(18):3826-3840.

Gamage, et al.; "Structure-activity relationships for substituted 9-oxo-9,10-dihydroacridine-4-acetic acids: analogues of the colon tumour active agent xanthenone-4-acetic acid"; Anti-Cancer Drug Design; (1992), 7(5):403-414.

Graham, et al.; Fresh from the Pipeline: Cetuximab; Nature Reviews Drug Discovery (2004), 3:549-550.

Griffioen, et al.; "Angiogenesis Inhibitors Overcome Tumor Induced Endothelial Cell Anergy"; Int. J. Cancer (1999), 80:315-319.

Hill, et al.; "Anti-Vascular Approaches to Solid Tumour Therapy: Evaluation of Vinblastine and Flavone Acetic Acid"; Int. J. Cancer (1995), 63(1):119-123.

Hornung, et al.; "Augmentation of Natural Killer Activity, Induction of IFN and Development Tumor Immunity During the Successful Treatment of Established Murine Renal Cancer Using Flavone Acetic Acid and IL-2"; The Journal of Immunology (1988), 141(10):3671-3679.

Jameson, et al.; "Clinical aspects of a phase I trial of 5,6-dimethylxanthenone-4-acetic acid (DMXAA), a novel antivascular agent"; British Journal of Cancer (2003), 88:1844-1850.

Jameson, et al.; "Phase I Pharmacokinetic and Pharmacodynamic Study of 5,6-Dimethylxanthenone-4-Acetic Acid (DMXAA), A Novel Antivascular Agent"; Proc. Am. Soc. Clin Oncol. (2000), 19: 182a.

Johnson, et al.; "Relationships between drug activity in NCI preclinical in vitro and in vivo models and early clinical trials"; British J. of Cancer (2001), 84(10):1424-1431.

Joseph, et al.; "Stimulation of Tumors to Synthesize Tumor Necrosis Factor-alpha in Situ Using 5,6-Dimethylxanthenone-4-acetic Acid: A Novel Approach to Cancer Therapy"; Cancer Res. (1999), 59(3):633-638.

Kanwar, et al.; "Taking lessons from dendritic cells: Multiple xenogeneic ligands for leukocyte integrins have the potential to stimulate anti-tumor immunity"; Gene Therapy (1999), 6:1835-1844.

Kanwar, et al.; "Vascular attack by 5, 6-dimethylxanthenone-4-acetic acid combined with B7.1 (CD80)- mediated immunotherapy overcomes immune-resistance and leads to the eradication of large tumors and multiple tumor foci"; Cancer Res. (2001), 61(5):1948-1956.

Kelland, L.; "Targeting Established Tumor Vasculature: A Novel Approach to Cancer Treatment"; Curr.Cancer. Ther. Rev. (2005), 1(1):1-9.

Kestell, et al.; "Determination of xanthenone-4-acetic acid in mouse plasma by high-performance liquid chromatography"; J. Chromatography (1991), 564(1):315-321.

Kestell, et al.; "Disposition of the novel antitumour agent xanthenone-4-acetic acid in the mouse: identification of metabolites and routes of elimination"; Xenobiotica (1994), 24(7):635-647.

Kestell, et al.; "Plasma disposition, metabolism and excretion of the experimental antitumour agent 5,6-dimethylxanthenone-4-acetic acid in the mouse, rat and rabbit"; Cancer Chemother. Pharmacol. (1999), 43(4):323-330.

Kestell, et al.; "Modulation of the pharmacokinetics of the antitumour agent 5,6-dimethylxanthenone-4-acetic acid (DMXAA) in mice by thalidomide"; Cancer Chemother. Pharmacol (2000), 46(2):135-141.

Kroll, et al.; "Improving Drug Delivery to Intracerebral Tumor and Surrounding Brain in a Rodent Model: A Comparison of Osmotic versus Bradykinin Modification of the Blood-Brain and/or Blood-Tumor Barriers"; Neurosurgery (1998), 43(4):879-886.

Langer, R.; "New Methods of Drug Delivery"; Science (1990), 249:1527-1533.

Lash, et al.; "Enhancement of the anti-tumour effects of the antivascular agent 5,6-dimethylxanthenone-4-acetic acid (DMXAA) by combination with 5-hydroxytryptamine and bioreductive drugs"; Br. J. Cancer (1998), 78(4):439-445.

Laws, et al.; "Preclinical in vitro and in vivo activity of 5,6-dimethylxanthenone-4-acetic acid"; British Journal of Cancer; (1995), 71(6):1204-1209.

Lissoni, et al.; "Neuroimmunotherapy of advanced solid neoplasms with single evening subcutaneous injection of low-dose interleukin-2 and melatonin: Preliminary results"; European Journal of Cancer (1993), 29A(2):185-189.

Maier, et al.; "In-Vitro inhibition of endothelial cell growth by the antiangiogenic drug AGM-1470, (TNP-470) and the anti-endoglin antibody TEC-11"; Anti-Cancer Drugs (1997), 8:238-244.

Marnett, L.J.; "Aspirin and Related Nonsteroidal Anti-inflammatory Drugs as Chemopreventive Agents against Colon Cancer"; Preventive Medicine 24,103-106 (1995).

Marona, H.; "Synthesis and Properties of Some Xanthone-2-Alkylcarboxylic acids and Xanthone-2-Glyoxal"; Polish Journal of Chemistry, 54:2059 (1980).

McKeage, et al.; "5,6-Dimethylxanthenone-4-Acetic Acid in the Treatment of Refractory Tumors: a Phase I Safety Study of a Vascular Disrupting Agent"; Clin. Cancer Res. (2006), 12(6):1776-1784.

McKeage, et al.; "Plasma pharmacokinetics of the antitumour agents 5,6-dimethylxanthenone-4-acetic acid, xanthenone-4-acetic acid and flavone-8-acetic acid in mice"; Cancer Chemother. Pharmacol.; (1991) 28(6), 409-413.

McLachlan, et al.; "The Potential of Cyclosporin A as an Anti-Tumour Agent"; Int. J. Immun. (1990), 12(5):469-479.

Miners, et al.; "Preclinical Prediction of Factors Influencing the Elimination of 5,6-Dimethylxanthenone-4-acetic Acid, a New Anticancer Drug"; Cancer Research (1997), 57(2):284-289.

Moilanen, et al.; "Persistent induction of nitric oxide synthase in tumours from mice treated with the anti-tumour agent 5,6-dimethylxanthenone-4-acetic acid"; British Journal of Cancer (1998), 77(3): 426-433.

Murata, et al.; "Comparative effects of combretastatin A-4 disodium phosphate and 5, 6-dimethylxanthenone-4-acetic acid on blood perfusion in a murine tumour and normal tissues"; Int. J. Radiat. Biol. (2001), 77(2):195-204.

Nakamura, et al.; "Antitumor Effect of Recombinant Human Interleukin 1 Alpha against Murine Syngeneic Tumors"; Jpn. J. Cancer Research (Gann) (1986), 77:767-773.

Nakanishi, et al.; "Carboxylic Acids"; Chem. Abstr. 76:126784w (1972), (Abstract of Japan A-7,200,425).

Nakanishi, et al.; "Studies of Anti-Inflammatory Agents XXXI; Studies on the Synthesis and Anti-Inflammatory Activity of Xanthenyl- and Benzo-pyranopyridinylacetic acid Derivatives"; Yakugaku Zasshi (1976), 96:99-109.

Nawrocki, et al.; "Genetically modified tumour vaccines—where we are today"; Cancer Treatment Reviews (1999), 25:29-46.

Neuwelt, et al.; "Increased Delivery of Tumor-specific Monoclonal Antibodies to Brain after Osmotic Blood-Brain-Barrier modification in Patients with Melanoma Metastatic to the Central Nervous System"; Neurosurgery (1987), 20(6):885-895.

Nishino, et al.; "Oxidation of 9-Xanthenones with Lead (IV) Acetate. Formation of Di-gamma-lactones"; Bull. Chem Soc. Jpn. (1983), 56:2847-48.

Nishino, et al.; "Regioselective Carboxylation of 9-Xanthenones with Manganese (III) Acetate." Bull. Chem Soc. Jpn. (1983), 56:474-480.

O'Reilly, et al.; "Endostatin: An Endogenous Inhibitor of Angiogenesis and Tumor Growth"; Cell (1997), 88:277-285.

Pang, et al.; "Antitumour Activity of the Novel Immune Modulator 5, 6-Dimethylxanthenone-4-acetic Acid (DMXAA) in Mice Lacking the Interferon-gamma Receptor"; European Journal of Cancer (1998), 34(8):1282-1289.

Patel, et al.; "The Effect of 5, 6-Dimethylxanthenone-4-acetic acid on Tumour Necrosis Factor Production by Human Immune Cells"; Anti-cancer Research (1997), 17(1A):141-150.

Peckham, et al.; "Oxford Textbook of Oncology". Oxford University Press, vol. 1. p. 451, 1995.

Pedley, et al.; "Ablation of Colorectal Xenografts with Combined Radioimmunotherapy and Tumor Blood Flow-modifying Agents"; Cancer Research (1996), 56(14):3293-3300.

Pedley, et al.; "Enhancement of Radioimmunotherapy by Drugs Modifying Tumour Blood Flow in a Colonic Xenograft Model"; Int. J. Cancer (1994), 57(6):830-835.

Pedley, et al.; "Enhancement of antibody-directed enzyme prodrug therapy in colorectal xenografts by an antivascular agent"; Cancer Res. (1999), 59(16):3998-4003.

Perera, et al.; "Activation of LPS-Inducible Genes by the Antitumor Agent 5,6-Dimethylxanthenone-4-Acetic Acid in Primary Murine Macrophages"; The Journal of Immunology (1994), 153(10):4684-4693.

Phillips, R.M.; "Inhibition of DT-diaphorase (NAD(P)H:quinone oxidoreductase, EC 1.6.99.2) by 5,6-dimethylxanthenone-4-acetic acid (DMXAA) and flavone-8-acetic acid (FAA): Implications for bioreductive drug development"; Biochem. Pharmacol. (1999), 58(2):303-310.

Philpott, et al.; "Production of tumour necrosis factor-alpha by cultured human peripheral blood leukocytes in response to the anti-tumour agent 5, 6-dimethylxanthenone-4-acetic acid (NSC 640488)"; British Journal of Cancer (1997), 76(12):1586-1591.

Plowman, et al.; "Flavone Acetic Acid: A Novel Agent with Preclinical Antitumor Activity Against Colon Adenocarcinoma 38 in Mice"; Cancer Treatment Reports (1986), 70(5):631-635.

Pruijn, et al.; "Mechanisms of enhancement of the antitumour activity of melphalan by the tumour-blood-flow inhibitor 5, 6-dimethylxanthenone-4-acetic acid"; Cancer Chemother. Pharmacol. (1997), 39(6):541-546.

Rewcastle, et al.; "Light-Induced Breakdown of Flavoneacetic Acid and Xanthenone Analogues in Solution"; J. Natl. Cancer Inst. (1990), 82(6):528-529.

Rewcastle, et al.; "Potential Antitumor Agents. 58. Synthesis and Structure-Activity Relationships of Substituted Xanthenone-4-acetic Acids Active against the Colon 38 Tumor in Vivo"; J. Med. Chem. (1989), 32(4):793-799.

Rewcastle, et al.; "Potential Antitumor Agents. 61. Structure-Activity Relationships for in Vivo Colon 38 Activity among Disubstituted 9-oxo-9H-xanthene-4-acetic Acids"; J. Med. Chem. (1991), 34(1):217-222.

Rewcastle, et al.; "Potential Antitumor Agents. 62. Structure-Activity Relationships for Tricyclic Compounds Related to the Colon Tumor Active Drug 9-Oxo-9H-xanthene-4-acetic Acid"; J. Med. Chem. (1991), 34:491-496.

Rewcastle, et al.; "Potential Antitumor Agents. 63. Structure-Activity Relationships for Side-Chain Analogues of the Colon 38 Active Agent 9-oxo-9H-xanthene-4-acetic Acid"; J. Med. Chem. (1991), 34(9):2864-2870.

Rewcastle, G. W.; "Synthesis and Development of Two New Classes of Anticancer Drugs: the tricyclic Carboxamides and the xanthenoneacetic acids"; Chemistry in New Zealand (1989),.53(6):145-150.

Rieckmann, et al.; "Okadaic Acid is a potent inducer of AP-1, NF-kappa-B, and Tumor-Necrosis Factor-alpha in Human B Lymphocytes"; Biochem. Biophys. Res. Commun. (1992), 187(1):51-57.

Rustin et al.; "5,6-Dimethylxanthenone-4-acetic acid (DMXAA), a novel antivascular agent: phase I clinical and pharmacokinetic study"; British Journal of Cancer (2003), 88:1160-1167.

Rustin et al.; "Impact on Tumour Perfusion Measured by Dynamic Magnetic Resonance Imaging (MRI), in the Phase 1 Trial of 5,6-dimethylxanthenone-4-aceticAcid (DMXAA)"; Proc. 10th NCI-EORTC Symp. New Drugs (1998), 10:126.

Rustin, G.; "Vascular Targeting in the Clinic"; Abstract; ICTR 2000: 1st Int'l Conference on Translational Research A., 2000.

Saltiel, E.; "Erlotinib". Http://www.medicinenet.com/erlotinib/article.htm. Nov 28, 2004.

Saltiel, E.; "Gefitinib". Http://www.medicinenet.com/gefitinib/article.htm. Jun. 22, 2005.

Sausville, et al.; "Contributions of human tumor xenografts to anti-cancer drug development"; Cancer Research (2006), 66(7):3351-3354.

Shoemaker, et al.; "Pleiotropic Resistance and Drug Development"; Cancer Drug Resistance (1986), 143-149.

Showalter, H.; "Potential Antitumor Agents. 61. Structure-Activity Relationships for In Vivo Colon 38 Activity Among Disubstituted 9-Oxo-9H-xanthene-4-acetic acids"; Chemtracts: Org. Chem. (1991), 4(2): 168-171. Commentary of Rewcastle: J. Med. Chem. (1991), 34:217-222.

Siemann, et al.; "Enhanced Antitumor Efficacy through the combination of Vascular Targeting Agents and Conventional Anticancer Drugs"; Proceedings of the American Association for Cancer Research (2000), 41:525.

Siemann, et al.; "Vascular Targeting Agents Enhance Chemotherapeutic Agent Activities in Solid Tumor Therapy"; Int. J. Cancer (2002), 99:1-6.

Siim, et al.; "Marked potentiation of the antitumour activity of chemotherapeutic drugs by the antivascular agent 5,6-dimethylxanthenone-4-acetic acid (DMXAA)"; Cancer Chemother Pharmacol (2003), 51:43-52.

Siim, et al.; "Nitro Reduction as an Electronic Switch for Bioreductive Drug Activation"; Oncology Research (1997), 9(6/7):357-369.

Siim, et al.; "Scintigraphic Imaging of the Hypoxia Marker 99m-Technetium-labeled 2,2'-(1,4- Diaminobutane)bis(2-methyl-3-butanone) Dioxime (99mTc-labeled HL-91; Prognox): Noninvasive Detection of Tumor Response to the Antivascular Agent 5, 6-Dimethylxanthenone-4-acetic Acid"; Cancer Research (2000), 60(16):4582-4588.

Temsamani, et al.; "Brain drug delivery technologies: novel approaches for transporting therapeutics"; Pharm. Sci. Technology Today (2000), 3(5):155-162.

Thomsen, et al.; "Evidence for the Production of Nitric Oxide by Activated Macrophages Treated with the Antitumor Agents Flavone-8-acetic Acid and Xanthenone-4-acetic Acid"; Cancer Research (1990), 50(21):6966-6970.

Thomsen, et al.; "Modulation of superoxide production from murine macrophages by the antitumour agent flavone acetic acid and xanthenone acetic acid analogues"; Biochemical Pharmacology (1992), 43(2):386-389.

Thomsen, et al.; "Nitric Oxide: its production in host-cell-infiltrated EMT6 spheroids and its role in tumor cell killing by flavone-8-acetic acid and 5, 6-dimethylxanthenone-4-acetic acid"; Cancer Chemother. Pharmacol. (1992), 31(2):151-155.

Thomsen, et al.; "Nitric Oxide Production in endotoxin-resistant C3H/HeJ mice stimulated with flavone-8-acetic acid and xanthenone-4-acetic acid analogues"; Biochem. Pharmacol. (1992), 43(11):2401-2406.

Thomsen, et al.; "Tumor-dependent increased plasma nitrate concentrations as an indication of the antitumor effect of flavone-8-acetic acid and analogues in mice"; Cancer Res. (1991), 51(1):77-81.

Thrash-Bingham, et al.; "aHIF: A natural antisense transcript overexpressed in human renal cancer during hypoxia"; The Journal of the National Cancer Institute (1999), 91(2):143-151.

Tyle, P.; "Iontophoretic Devices for Drug Delivery"; Pharmaceutical Research (1986), 3(6):318-326.

Van Der Auwera, et al.; "Conformational Features of Four Model Tripeptides Having Piv-Pro-MeXaa-NMe2 Sequences"; Bull. Soc. Chim. Belg. (1988), 97(3):199-207.

Van Moorsel, et al.; "Combination Chemotherapy Studies with Gemcitabine and Etoposide in Non-Small Cell Lung and Ovarian Cancer Cell Lines"; Biochemical Pharmacology (1999), 57:407-415.

Veszelovszky, et al.; "Flavone Acetic Acid and 5, 6-Dimethylxanthenone-4-acetic Acid: Relationship between Plasma Nitrate Elevation and the Induction of Tumour Necrosis"; Eur. J. Cancer, Part A (1993), 29A(3): 404-408.

Vincent, et al.; "Chemotherapy with DMXAA (5, 6-dimethylxanthenone-4-acetic acid) in combination with CI-1010 (1H-imidazole-1-ethanol, alpha-[[(2-bromoethyl)amino]methyl]-2-nitro-, mono-hydrobromide (R isomer)) against advanced stage murine colon carcinoma 26"; Oncology Reports (1997), 4(1):143-147.

Watts, et al.; "Changes in coagulation and permeability properties of human endothelial cells in vitro induced by TNF-alpha or 5,6 MeXAA"; British Journal of Cancer, Suppl. (1996), 74(27):S164-S167.

Webster, et al.; "Metabolism and Elimination of 5,6-Dimethylxanthenone-4-Acetic Acid in the Isolated Perfused Rat Liver"; Drug Metabolism and Disposition (1995), 23(3):363-368.

Westland, et al.; "Activated non-neural specific T cells open the blood-brain-barrier to circulating antibodies"; Brain (1999), 122:1283-1291.

Wiesenthal. "Is one 'sensitive' drug better than another? Can you detect drug synergy? What are the best drug combinations?" http://weisenthal.org/feedback.html, Feb. 4, 2002.

Wilson, et al.; "Combination of the Antivascular Agent DMXAA with Radiation and Chemotherapy", International Journal of Oncology, Biology and Physics (2000), 46(3):706, [abstract 46].

Wilson, et al.; "Enhancement of Tumor Radiation Response by the Antivascular Agent 5,6- Dimethylxanthenone-4-Acetic Acid"; Int. J. Radiation Oncology Biol. Phys. (1998), 42(4):905-908.

Wilson, et al.; "Tertiary amine N-oxides as bioreductive drugs: DACA N-oxide, nitracrine N-oxide and AQ4N"; British Journal of Cancer Supplemental (1996), 74(27):S43-S47.

Wilson, et al.; "Hypoxia-Activated Prodrugs as Antitumour Agents: Strategies for Maximizing Tumor Cell Killing"; Clinical and Experimental Pharmacology and Physiology (1995), 22(11):881-885.

Wouters, et al.; "Hypoxia as a target for combined modality treatments"; European J. Cancer (2002), 38:240-257.

Zaharko, et al.; "Therapeutic and Pharmacokinetic Relationships of Flavone Acetic Acid: An Agent with Activity Against Solid Tumors"; Cancer Treatment Reports (1986), 70(12):1415-1421.

Zaks-Zilberman, et al.; "Induction of Adrenomedullin mRNA and Protein by Lipopolysaccharide and Paclitaxel (Taxol) in Murine Macrophages"; Infection and Immunity (1998), 66(10):4669-4675.

Zhang, et al.; "Conjugation of brain-derived neurotrophic factor to a blood-brain-barrier resistant drug targeting system enables neuroprotection in reginal brain ischemia following intravenous injection of the neurotrophin"; Brain Research (2001), 889:49-56.

Zhao, et al.; "Effects of the serotonin receptor antagonist cyproheptadine on the activity and pharmacokinetics of 5, 6-dimethylxanthenone-4-acetic acid (DMXAA)"; Cancer Chemother. Pharmacol. (2001), 47(6):491-497.

Zhou, et al.; "5,6-dimethylxanthenone-4-acetic acid (DMXAA): a new biological response modifier for cancer therapy"; Invest New Drugs. (2002), 20(3):281-95.

Zhou, et al.; "Determination of the covalent adducts of the novel anti-cancer agent 5, 6- dimethylxanthenone-4-acetic acid in biological samples by high-performance liquid chromatography"; J. Chromatography B (2001), 757:343-348.

Zhou, et al.; "Determination of unbound concentration of the novel anti-tumour agent 5,6-dimethylxanthenone-4-acetic acid in human plasma by ultrafiltration followed by high-performance liquid chromatography with fluorimetric detection"; J. Chromatography B (2001), 757(2):359-363.

Zhou, et al.; "Effects of anticancer drugs on the metabolism of the anticancer drug 5,6-dimethylxanthenone-4-acetic (DMXAA) by human liver microsomes"; J. Clin. Pharmacol. (2001), 52:129-136.

Zhou, et al.; "Reversible binding of the novel anti-tumour agent 5,6-dimethylxanthenone-4-acetic acid to plasma proteins and its distribution into blood cells in various species"; J. Pharmacy Pharmacology (2001), 53(4):463-471.

Zhou, et al.; "A difference between the rat and mouse in the pharmacokinetic interaction of 5, 6-dimethylxanthenone-4-acetic acid with thalidomide"; Cancer Chemother. Pharmacol. (2001), 47(6):541-544.

Zhou, et al.; "Determination of two major metabolites of the novel anti-tumor agent 5, 6-dimethylxanthenone-4-acetic acid in hepatic microsomal incubations by high-performance liquid chromatography with fluorescence detection"; J. Chromatography B (1999), 734(1):129-136.

Zhou, et al.; "Identification of the Human Liver Cytochrome P450 Isoenzyme Responsible for the 6-Methylhydroxylation of the Novel Anticancer Drug 5, 6-Dimethylxanthenone-4-Acetic Acid"; Drug Metabolism and Disposition (2000), 28(12):1449-1456.

Zhou, et al.; "In vitro and in vivo kinetic interactions of the antitumour agent 5, 6-dimethylxanthenone-4-acetic acid with thalidomide and diclofenac"; Cancer Chemother. Pharmacol; (2001), 47(4):319-326.

Zitvogel, et al.; "Interleukin-12 and B7.1 co-stimulation cooperate in the induction of effective antitumor immunity and therapy of established tumors"; Eur. J. Immunol. (1996), 26:1335-1341.

Zwi, et al.; "Blood Flow Failure as a Major Determinant in the Antitumor Action of Flavone Acetic Acid"; J. Natl. Cancer Inst. (1989), 81:1005-1013.

Zwi, et al.; "Necrosis in non-tumour tissues caused by flavone acetic acid and 5,6-dimethyl xanthenone acetic acid"; Br. J. Cancer (1990), 62(6): 932-934.

Zwi, et al.; "The Morphological Effects of the Anti-Tumor Agents Flavone Acetic Acid and 5,6-Dimethyl Xanthenone Acetic Acid on the Colon 38 Mouse Tumor"; Pathology (1994), 26(2):161-169.

Zwi, et al.; "Correlation between immune and vascular activities of xanthenone acetic acid antitumor agents"; Oncol. Res. (1994), 6(2):79-85.

* cited by examiner

ANTI-CANCER COMPOSITION COMPRISING DMXAA OR RELATED COMPOUND

RELATED APPLICATIONS

This application is a continuation of International Application No. PCT/GB03/004688 which was filed on 30 Oct. 2003, which designated the United States and was published in English, and which claims the benefit of United Kingdom Application No. GB0225508.1, filed 1 Nov. 2002, the entirety of which is incorporated herein by reference.

The present invention relates to pharmaceutical compositions and their use in therapy, particularly in the treatment of cancers. In particular, the present invention relates to formulations of anticancer compositions which can be delivered gastrointestinally, for example orally, and to a method of treatment of cancer, in which the anticancer compositions are delivered gastrointestinally, such as orally. More in particular, the present invention relates to the progressive or sequential delivery or release of gastrointestinally administered compounds of the class having the formula (I) as defined below, for example compounds of the xanthenone acetic acid class having the formula (II) as defined below, such as 5,6-dimethylxanthenone-4-acetic acid (DMXAA).

The use of drugs in systemic chemotherapy has provided effective management of some cancer types. For example, systemic chemotherapy has been used successfully in the treatment of cancers of the colon-rectum, oesophagus, liver, pancreas, kidney and skin. Prolonged periods of therapy may be required in cancer patients to control tumour growth and, in some instances, prevent the growth of secondary malignancies. Anti-cancer drugs having poor bioavailability are required in high doses to maintain their efficacy. As a result the continuing administration of high dosages of systemic therapeutic agents may be required to provide efficacious amounts of chemotherapeutic agents.

A major problem with systemic chemotherapy for the treatment of cancer is that the systemic dose levels required for controlling tumour growth frequently result in unacceptable systemic toxicity. For example, although paclitaxel (Taxol™, Bristol Myers Squibb) has been used systemically with efficacy in treating several human tumours, including ovarian, breast, and non-small cell lung cancer, maintenance of sufficient systemic levels for tumour efficacy has been associated with severe, in some cases "life-threatening" toxicity (Sarosy and Reed, J. Nat. Med. Assoc. 85(6):427-431 (1993).

There has been an increasing trend toward the development of oral systemic chemotherapeutic agents having improved efficacy and bioavailability for the treatment of patients with a variety of malignancies. Chemotherapy administered gastrointestinally, provides social, economic and medical benefits. For example, the cost of treatment is usually far lower compared to intravenous administration and gastrointestinal administration (particularly oral or rectal administration) is more convenient for patients, permitting them to remain at home while taking their medications and eliminating the need for venous access, which may require the presence of a physician and/or nurse and/or a prolonged stay in hospital. However, despite the desirability of developing an orally active treatment, to date there has been little success in doing so for many otherwise useful anticancer agents.

In particular, to date, there has been no successful demonstration of tumour treatment using gastrointestinally, for example orally, administered xanthenone acetic acid compounds, such as DMXAA (5,6-dimethylxanthenone-4-acetic acid). DMXAA is an effective drug with an anti-vascular action. DMXAA is represented by the following formula:

Phase I clinical trials of DMXAA have recently been completed, with dynamic MRI showing that it induces a significant reduction in tumour blood flow at well-tolerated doses. DMXAA is thus one of the first antivascular agents for which activity (irreversible inhibition of tumour blood flow) has been documented in human tumours. These findings are in agreement with preclinical studies using tumours or human tumour xenografts which showed that its antivascular activity produced prolonged inhibition of tumour blood flow leading to extensive regions of haemorrhagic necrosis within the tumour.

Preclinical studies have demonstrated the utility of combining DMXAA with other agents including thalidomide, radiation therapy, bioreductive agents, cytotoxic drugs and radioimmunotherapy. However, typically, the administration of DMXAA in preclinical trials has been restricted to intraperitoneal (i.p) and intravenous (i.v) injection. Orally administered DMXAA has shown only limited antitumour activity. Zhao et al (Cancer Chemother Pharmacol. 2002 January; 49(1):20-6) describes the administration of DMXAA orally and reports that the antitumour effect, as measured by delay in tumour growth achieved with a single dose of orally administered DMXAA is low compared to that achieved when DMXAA was administered intraperitoneally. Indeed, no cures were obtained using the orally administered DMXAA compared to 40% for intraperitoneal administration. Moreover, repeated dosing of DMXAA administered intraperitoneally over a 24 hour period was not found to be superior to administration of a single dose.

There is therefore a need to provide a composition and method of use for the treatment of solid tumours with chemotherapeutic agents such as DMXAA that avoids high systemic levels of the agent and associated toxicities and which offers the social, medical and economic benefits of gastrointestinal delivery.

SUMMARY OF THE INVENTION

It has now surprisingly been found that, contrary to the teaching of the prior art, by administering compounds having the formula (I) as defined below in sequential gastrointestinally administered doses, potentiation of the antitumour activity of compounds of formula (I) compared to that achieved when a single dose is administered is nevertheless achieved. In particular administration of compounds of formula (I) as defined below such as DMXAA administered in a dosing regimen of a first high oral dose (approximately corresponding to the maximum tolerated dose) followed by one or more, preferably two or more, further oral doses within a 24 hour time frame has surprisingly been found to provide a therapeutic gain, as compared to the oral administration of the maximum tolerated single dose (MTD) against subcutaneously established colon tumour, without a concomitant increase in host toxicity.

The finding that such a therapeutic gain could be achieved using a sequential oral regime without associated serious toxicity was particularly surprising given that, using the area under concentration curve associated with the treatment regime as a predictor of toxicity, unacceptable side effects/toxic effects would be predicted. However, no such effects were seen, suggesting that, without being limited to any one explanation, toxicity of DMXAA and other compounds of the class of compounds of Formula (I) is related to maximum concentration and not the area under the concentration-time curve.

The present inventors findings thus enable the effective treatment of tumours using gastrointestinally administered, preferably orally administered DMXAA and other compounds of Formula (I) without high levels of toxicity and side-effects.

As described below, the present inventors have found that delay in growth of subcutaneous tumours can be induced using sequential oral administration of a xanthenone-4-acetic acid derivative. The present inventors findings thus enable the effective treatment of tumours using gastrointestinally administered DMXAA without high levels of toxicity and side-effects.

Accordingly, in a broad aspect, the present invention relates to the sequential gastrointestinal administration of a composition comprising a compound having the formula (I) as defined below for use in controlling tumour growth.

Thus, in a first aspect, the present invention provides a method for modulating neoplastic growth, which comprises gastrointestinally administering to a mammal, including a human, in need of treatment an effective amount of a compound of the formula (I):

Formula (I)

or a pharmaceutically acceptable salt or ester thereof, wherein said effective amount is delivered to its site of action in the mammal in two or more doses;

wherein:

(a) $R_4$ and $R_5$ together with the carbon atoms to which they are joined, form a 6-membered aromatic ring having a substituent —$R_3$ and a radical —(B)—COOH where B is a linear or branched substituted or unsubstituted $C_1$-$C_6$ alkyl radical, which is saturated or ethylenically unsaturated, and wherein $R_1$, $R_2$ and $R_3$ are each independently selected from the group consisting of H, $C_1$-$C_6$ alkyl, halogen, $CF_3$, CN, $NO_2$, $NH_2$, OH, OR, NHCOR, NHSO$_2$R, SR, SO$_2$R or NHR, wherein each R is independently $C_1$-$C_6$ alkyl optionally substituted with one or more substituents selected from hydroxy, amino and methoxy; or (b) one of $R_4$ and $R_5$ is H or a phenyl radical, and the other of $R_4$ and $R_5$ is H or a phenyl radical which may optionally be substituted, thenyl, furyl, naphthyl, a $C_1$-$C_6$ alkyl, cycloalkyl, or aralkyl radical; $R_1$ is H or a $C_1$-$C_6$ alkyl or $C_1$-$C_6$ alkoxy radical; $R_2$ is the radical —(B)—COOH where B is a linear or branched substituted or unsubstituted $C_1$-$C_6$ alkyl radical, which is saturated or ethylenically unsaturated.

Where the radical —(B)—COOH is a substituted $C_1$-$C_6$ alkyl radical, the substituents may be alkyl, for example methyl, ethyl, propyl or isopropyl, or halide such as fluoro, chloro or bromo groups. A particularly preferred substituent is methyl.

In one embodiment of the first aspect of the invention, the compound of the formula (I) as defined above is a compound of the formula (II), Formula (II)

where $R_1$, $R_4$, $R_5$ and B are as defined above for formula (I) in part (b).

In a preferred embodiment of the first aspect of the invention, the compound of formula (I) as defined above is a compound of the formula (III)

Formula (III)

wherein $R_1$, $R_2$ and $R_3$ are each independently selected from the group consisting of H, $C_1$-$C_6$ alkyl, halogen, $CF_3$, CN, $NO_2$, $NH_2$, OH, OR, NHCOR, NHSO$_2$R, SR, SO$_2$R or NHR, wherein each R is independently $C_1$-$C_6$ alkyl optionally substituted with one or more substituents selected from hydroxy, amino and methoxy;

wherein B is as defined for formula (I) above;

and wherein in each of the carbocyclic aromatic rings in formula (I), up to two of the methine (—CH═) groups may be replaced by an aza (—N═) group;

and wherein any two of $R_1$, $R_2$ and $R_3$ may additionally together represent the group —CH═CH—CH═CH—, such that this group, together with the carbon or nitrogen atoms to which it is attached, forms a fused 6 membered aromatic ring.

Preferably, the compound of formula (III) is a compound of the formula (IV):

Formula (IV)

wherein R, $R_1$, $R_2$ and $R_3$ are as defined for formula (III).

In a preferred embodiment of the compound of formula (IV), $R_2$ is H, one of $R_1$ and $R_3$ is selected from the group consisting of $C_1$-$C_6$ alkyl, halogen, $CF_3$, CN, $NO_2$, $NH_2$, OH, OR, NHCOR, $NHSO_2R$, SR, $SO_2R$ or NR wherein each R is independently $C_1$-$C_6$ alkyl optionally substituted with one or more substituents selected from hydroxy, amino and methoxy, and the other of $R_1$ and $R_3$ is H.

Preferably, the compound of formula (IV) is of the formula (V):

Formula (V)

wherein R, $R_1$, $R_2$ and $R_3$ are as defined for formula IV.

Most preferably, the compound of formula (IV) is 5,6-dimethylxanthenone 4 acetic acid (DMXAA).

In a further aspect, the present invention provides a compound of formula (I) as defined above for use in the prevention or treatment of cancer; wherein the compound is provided in a composition for sequential gastrointestinal administration, and wherein, in use, an effective therapeutic amount of said compound is delivered to a site of action over two or more doses.

In another aspect, the present invention provides the use of a compound of formula (I) as defined above or a pharmaceutically acceptable salt or ester thereof for the manufacture of a medicament, for gastrointestinal administration, for the modulation of neoplastic growth, wherein, said medicament is delivered to its site of action in the mammal in two or more doses.

In preferred embodiments of the invention, the two or more doses are provided as separate dosage forms for sequential administration to the mammal in need thereof, with a time interval between administration of the doses.

In alternative embodiments of the invention, the two or more doses are provided in a single dosage form, such as a controlled release formulation, for administration to the mammal in need thereof, which, in use releases the individual doses at different times, with a time interval between successive releases of doses.

In preferred embodiments of the invention, the route of gastrointestinal administration is oral administration.

As used herein the phrase "preparation of a medicament" includes the use of a compound of the invention directly as the medicament in addition to its use in a screening programme for the identification of further agents or in any stage of the manufacture of such a medicament.

By "therapeutically effective amount" is meant an amount of the compound formula (I) or one of its salts that when administered gastrointestinally, preferably orally, alone or in combination formulation such that the compound is delivered to a site of action in two or more doses is effective to treat the various disorders for which the compound having formula (I) as defined above has been disclosed as a useful treatment.

The compound of formula (I), or pharmaceutically acceptable salt or ester thereof may be administered in any suitable form. However, for use according to the present invention the compound of formula (I) or a pharmaceutically acceptable salt or ester thereof is preferably presented as a pharmaceutical formulation. Pharmaceutical formulations comprise the active ingredient (that is, the compound of formula (I) or a pharmaceutically acceptable salt or ester thereof) together with one or more pharmaceutically acceptable carriers therefor and optionally other therapeutic and/or prophylactic ingredients. The carrier(s) must be acceptable in the sense of being compatible with the other ingredients of the formula and not deleterious to the recipient thereof.

Accordingly, in a further aspect there is provided a pharmaceutical formulation comprising a compound of formula (I) as defined above or a pharmaceutically acceptable salt or ester thereof wherein said pharmaceutical formulation is adapted for gastrointestinal, preferably oral, administration. Preferably said compound and/or pharmaceutical formulation is adapted for delivery of the active compound to its site of action in a mammal in need thereof in two or more doses, preferably two or more discrete doses.

In one preferred embodiment, said pharmaceutical formulation comprises said compound at an amount which, when administered as a single oral dose, is therapeutically ineffective, but, when the same total amount is administered by providing two or more sequential smaller oral doses, is therapeutically effective. Suitably, the smaller doses themselves are not effective if administered individually but are effective when administered sequentially to make up the total amount.

By "therapeutically ineffective amount" is meant an amount of the compound of the invention or one of its salts that, when administered as a single dose, is not effective to treat the various disorders for which the compound having formula (I) as defined above has been disclosed as a useful treatment or is such that, although a therapeutically effective result may be achieved, the amount is greater than the maximum tolerated dose and/or the associated side effects are unacceptable i.e. not acceptable to the patients, the doctor(s) in charge of treatment or regulatory bodies such as the U.S. Food and Drug Administration.

Said sequential doses are separated by a time interval, the calculation of which is preferably based on the plasma half-life ($t_{1/2}$) of the drug. The time interval is preferably approximately equal to one half-life of the drug, for example in the range 50% $t_{1/2}$ to 150% $t_{1/2}$, preferably in the range 70% $t_{1/2}$ to 130% $t_{1/2}$, more preferably in the range 80% $t_{1/2}$ to 120% $t_{1/2}$, even more preferably in the range 90% $t_{1/2}$ to 110% $t_{1/2}$, most preferably in the range 95% $t_{1/2}$ to 100% $t_{1/2}$. For example, the time interval is preferably greater than 1 hour, preferably greater than 2 hours, more preferably greater than 3 hours. Preferably said doses are separated by a time interval of less than 24 hours, for example, 4 hours, 6 hours or 8 hours.

In a further preferred embodiment of the invention, the pharmaceutical formulation is a controlled release formulation, wherein, in use, said formulation releases two or more doses, preferably at least two or more doses separated by a time interval between each dose. Preferably, each of said doses is such that, when administered as a single dose, it would be ineffective, but, when administered in two or more sequential doses is therapeutically effective.

Preferably said doses are released from said controlled release formulation with a time interval as described above for sequential doses. In a preferred embodiment, the time interval is at least one hour, more preferably at least two hours, most preferably at least four hours between doses. In a particularly preferred embodiment, the time interval is between 1 and 6 hours.

In a preferred embodiment, the invention further provides a process for the preparation of a pharmaceutical formulation comprising a compound of formula (I) as defined above wherein said process comprises bringing into association at least one unit dose and, optionally, one or more further unit doses of a compound of formula (I) as defined above or a pharmaceutically acceptable salt or ester thereof with one or more pharmaceutically acceptable carriers therefor, wherein said formulation is adapted for gastrointestinal, preferably oral, administration. Preferably said pharmaceutical formulation is adapted for delivery of the active compound to its site of action in a mammal in need thereof in two or more doses, preferably two or more discrete doses.

In a preferred embodiment, the process comprises bringing into association a first unit dose of a compound of formula (I) as defined above or a pharmaceutically acceptable salt or ester thereof with at least one further unit dose of a compound of formula (I) as defined above or a pharmaceutically acceptable salt or ester thereof and one or more pharmaceutically acceptable carriers therefor wherein, on administration to an individual, said first unit dose and said further unit doses are released from the formulation in discrete doses separated by a time interval.

According to a further aspect of the present invention, there is provided a pharmaceutical pack comprising two or more compartments wherein at least two compartments each house at least one dose each of the compound of formula I as defined above which may be in admixture with one or more of: a pharmaceutically acceptable carrier, diluent or excipient (or combinations thereof), an adjuvant or a pharmaceutically active agent, and wherein each dose of the compound of formula I are for administration in sequential gastrointestinal, preferably oral doses, preferably separated by a time interval. Preferably, said time interval is as described above.

The pack of the present invention may comprise a further compartment which houses a pharmaceutically acceptable carrier, diluent or excipient Furthermore, the invention also provides a kit comprising in combination for separate or sequential use in modulating neoplastic growth, a first unit dose of a compound of formula (I) as defined above or a pharmaceutically acceptable salt or ester thereof and at least one further unit dose of said compound or pharmaceutically acceptable salt or ester thereof, wherein said first and second unit doses are for gastrointestinal, preferably oral administration.

Compounds

Compounds of formula (I) and (II) may be prepared by methods known in the art. For instance, compounds of formula (I), wherein $R_1$, $R_2$, $R_3$, and $R_4$, are as defined in part (b) of the definition of formula (I) as recited above, may be prepared using the methods as disclosed in U.S. Pat. No. 4,602,034 (Briet et al), the contents of which are herein incorporated by reference.

Compounds of formula (III), (IV) and (V) are known and may be prepared using the methods known in the art. For example, compounds of formula (III), (IV) and (V) and their preparation are described in the following references, the contents of which are herein incorporated by reference:

Rewcastle et al, Journal of Medicinal Chemistry 34(1): 217-22, January 1991;
Rewcastle et al, Journal of Medicinal Chemistry 34(2): 491-6, February 1991;
Atwell et al, Journal of Medicinal Chemistry 33(5): 1375-9, May 1990;
Rewcastle et al, Journal of Medicinal Chemistry 34(9): 2864-70, September 1991;
Rewcastle et al, Journal of Medicinal Chemistry 32(4): 793-9, April 1989

DMXAA may be prepared according to the methods described in Rewcastle et al, Journal of Medicinal Chemistry 34(1): 217-22, January 1991, the contents of which are incorporated herein by reference.

Pharmaceutical Salts

The compounds used in the present invention may be administered as pharmaceutically acceptable salts. Typically, a pharmaceutically acceptable salt may be readily prepared by using a desired acid or base, as appropriate. The salt may precipitate from solution and be collected by filtration or may be recovered by evaporation of the solvent Pharmaceutically-acceptable salts are well known to those skilled in the art, and for example include those mentioned by Berge et al, in J. Pharm. Sci., 66, 1-19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more acidic moieties are present, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

The compounds used in the present invention may exist in polymorphic form.

In addition, the compounds used in the present invention may contain one or more asymmetric carbon atoms and therefore exists in two or more stereoisomeric forms. Where a compound contains an alkenyl or alkenylene group, cis (E) and trans (Z) isomerism may also occur. The present invention includes use of the individual stereoisomers of the compound and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the agent or a suitable salt or derivative thereof. An individual enantiomer of the compound may also be prepared from a corresponding optically pure intermediate or by resolution, such as by H.P.L.C. of the corresponding racemate using a suitable chiral support or by fractional crystallization of the diastereoisomeric salts formed by reaction of the corresponding racemate with a suitable optically active acid or base, as appropriate.

The present invention also includes use of all suitable isotopic variations of the compound of Formula (I) or a pharmaceutically acceptable salt thereof. An isotopic variation of an compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the compound and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compound and pharmaceutically acceptable salts thereof, for example, those in which a radioactive isotope such as $^{3}H$ or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the compound of the present invention and pharmaceutically acceptable salts thereof this invention can generally be prepared by conventional procedures using appropriate isotopic variations of suitable reagents.

The terms used in the claims encompass one or more of the forms just mentioned.

Formulation

The component(s) of the present invention may be formulated into a pharmaceutical composition, such as by mixing with one or more of a suitable carrier, diluent or excipient, by using techniques that are known in the art.

Pharmaceutical Compositions

The compounds used in the present invention may be administered alone but will generally be administered as a pharmaceutical composition or formulation—e.g. when the components are in admixture with a suitable pharmaceutical excipient, diluent or carrier selected with regard to the intended route of administration and standard pharmaceutical practice. The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), buffers, flavouring agents, surface active agents, thickeners, preservatives (including antioxidants) and the like, and substances included for the purpose of rendering the formulation isotonic with the blood of the intended recipient.

Examples of suitable carriers include lactose, starch, glucose, methyl cellulose, magnesium stearate, mannitol, sorbitol and the like. Examples of suitable diluents include ethanol, glycerol and water.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Treatment/Therapy

As with the term "treatment", the term "therapy" includes curative effects, alleviation effects, and prophylactic effects. The treatment/therapy may be on humans or animals.

The compounds and compositions may be used to treat any cancer. For example, the compounds, formulations and methods of the present invention may be used to treat malignancy of any type including, for example, cancer of the lung, breast, testes, prostate, gut including colon, ovary, skin, kidney, pancreas, and lymphatic organs, cervix, liver, brain and leukaemias.

Administration

Any suitable means for gastrointestinal administration (delivery) may be used. For example, the compound may be delivered orally, rectally or, indeed, by naso-gastric tube. Preferably, the compounds are administered orally.

For example, the composition can be administered orally in one or more of the forms of tablets, capsules, ovules, elixirs, solutions or suspensions, which may contain flavouring or colouring agents, for immediate-, delayed-, modified-, sustained-, pulsed- or controlled-release applications.

If the pharmaceutical composition is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compound may be combined with various sweetening or flavouring agents, colouring matter or dyes, with emulsifying and/or suspending agents and with diluents such as water, ethanol, propylene glycol and glycerin, and combinations thereof.

Pharmaceutical formulations suitable for oral administration may, where appropriate, be conveniently presented in discrete dosage units and may be prepared by any of the methods well known in the art of pharmacy. All methods include the step of bringing into association the active ingredients with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of the active ingredients. A tablet may be made by compression or moulding, optionally with one or more accessory ingredients. Compressed tablets may be prepared by compressing in a suitable machine the active compounds in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredients, either alone or in admixture with one or more accessory ingredients, into the capsule shells and then sealing them in the usual manner. Cachets are analogous to capsules wherein the active ingredients together with any accessory ingredient(s) are sealed in a rice paper envelope. The compound of formula (I) or a pharmaceutically acceptable salt or ester may also be formulated as dispersible granules, which may for example be suspended in water before administration, or sprinkled on food. The granules may be packaged e.g. in a sachet.

The active ingredients may also be formulated as a solution or suspension for oral administration. Formulations suitable for oral administration wherein the carrier is a liquid may be presented as a solution or a suspension in an aqueous liquid or a non-aqueous liquid, or as an oil-in-water liquid emulsion.

The active ingredients may also be formulated as a solution or suspension suitable for administration via a naso-gastric tube.

Pharmaceutical formulations suitable for rectal administration wherein, for example, the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

It should be understood that in addition to the aforementioned carrier ingredients the pharmaceutical formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Controlled Release

Formulations for gastrointestinal administration include controlled release dosage forms e.g. tablets wherein the active ingredients are formulated in an appropriate release—controlling matrix, or are coated with a suitable release—controlling film.

For example, in a preferable embodiment, the compounds of the invention may be administered using controlled release dosage forms. Any suitable controlled dosage form known in the art may be used in the present invention. Examples of controlled release formulations include, but are not limited to delayed release, spaced release, time coat, timed release, delayed action, programmed release, extended action, layered-time action, and repeated action controlled dosage forms. Details of suitable controlled release formulations may be found, for example, in Krowczynski, Extended-Release Dosage Forms, 1987 (CRC Press, Inc.), Chien, Novel Drug Delivery Systems, 1992 (Marcel Dekker, Inc.) and Kydonieus, Controlled Release Technologies: Methods, Theory and Applications, 1980 (CRC Press, Inc.) and U.S. Pat. No. 6,174,873.

Controlled release drug delivery systems which may be used in the present invention may include, but are not limited to, feedback-regulated drug delivery systems, rate-preprogrammed drug delivery systems and activation-modulated drug delivery systems In feedback-regulated drug delivery systems, release of drug molecules from the delivery systems may be activated by a triggering event, such as a biochemical substance, in the body. The rate of drug release is then controlled by the concentration of triggering agent detected by a sensor in the feedback regulated mechanism. In rate-preprogrammed drug delivery systems, release of drug molecules from the delivery systems are "preprogranmed" at specific rate profiles, by, for example, controlling the molecular diffusion of drug molecules in and/or across the barrier medium within or surrounding the delivery system. In activation-modulated drug delivery systems, release of drug molecules from the delivery systems is activated by some physical, chemical or biochemical processes and/or facilitated by the energy supplied externally.

There are a number of controlled release drug formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs.

Enteric coatings (for example, hydroxypropylmethylcellulose phthalate, methacrylic acid-methacrylic acid ester copolymer, polyvinyl acetate-phthalate and cellulose acetate phthalate) may be used to coat a solid or liquid dosage form of the compounds according to the invention. Enteric coatings promote the compounds remaining physically incorporated in the dosage form for a specified period when exposed to gastric juice but to disintegrate in intestinal fluid for ready absorption.

Another type of useful oral controlled release structure, which may be used in the present invention, is a solid dispersion of one or more active ingredients in an inert carrier or matrix in the solid state prepared by the melting (fusion), solvent, or melting-solvent method Another controlled release dosage form is a complex between an ion exchange resin and a compound according to the invention.

Other controlled release technologies that may be used in the practice of this invention are quite varied. They include SODAS (Spheroidal Oral Drug Absorption System), IPDAS (Intestinal Protective Drug Absorption System), PRODAS (Programmable Oral Drug Absorption System), and DUREDAS (Dual Release Drug Absorption System) available from Elan Pharmaceutical Technologies, Dublin, Ireland.

SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. PRODAS is a family of multi particulate formulations utilizing combinations of immediate release and controlled release mini-tablets. DUREDAS is a bilayer tablet formulation providing dual release rates within the one dosage form.

IPDAS is a multi-particulate tablet technology that is used to enhance the gastrointestinal tolerability of potential irritant and ulcerogenic drugs. Controlled release characteristics of the individual beads may avoid high concentration of drug being both released locally and absorbed systemically. By using a combination of at least two types of beads, which release their respective drugs at different parts of the intestinal tract, release of separate doses separated by a time interval may be achieved.

IPDAS is composed of numerous high density controlled release beads. Each bead may be manufactured by a two step process that involves the initial production of a micromatrix with embedded compounds according to the invention and the subsequent coating of this micromatrix with polymer solutions that form a rate limiting semipermeable membrane in vivo. Should a fast onset of activity be necessary, immediate release granulate may be included in the tablet A second type of granulate, which is released later may be included to provide sequential delivery of doses.

MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. MODAS represents a very flexible dosage form in that both the inner core and the outer semipermeable membrane may be altered to suit the individual delivery requirements of a drug. In particular, the addition of excipients to the inner core may help to produce a micro environment within the tablet that facilitates more predictable release and absorption rates. The addition of an immediate release outer coating may allow for development of products, in which separate doses of drugs may be released.

PRODAS is a multi particulate drug delivery system, which, may be used in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. One value of PRODAS technology lies in the inherent flexibility to formulation whereby combinations of mini tablets, each with different release rates, are incorporated into one dosage form. As well as potentially permitting controlled absorption of separate doses over defined specific periods, this also may permit targeted delivery of drug to specific sites of absorption throughout the gastrointestinal tract. Combination products also may be possible using mini tablets formulated with different active ingredients.

DUREDAS is a bilayer tableting technology that may be used in the practice of the invention. DUREDAS was developed to provide for two different release rates, or dual release of a drug from one dosage form. The term bilayer refers to two separate direct compression events that take place during the tableting process. In a preferable embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. Hence one layer of the tablet may be formulated as an immediate release granulate. By contrast, the second layer of the tablet may release the drug in a controlled manner, preferably through the use of hydrophilic polymers. This controlled release may result from a combination of diffusion and erosion through the hydrophilic polymer matrix.

A further extension of DUREDAS technology is the production of controlled release combination dosage forms. In this instance, two different compounds according to the invention may be incorporated into the bilayer tablet and the release of drug from each layer controlled to maximize therapeutic affect of the combination.

Dose Schedule

Typically, a physician will determine the actual dosage which will be most suitable for an individual subject. The specific dose level and frequency of dosage for any particular patient may be varied and will depend upon a variety of factors including the nature of the cancer, the therapy sought, the severity of the disease, the degree of malignancy, the extent of metastatic spread, the tumour load, general health status, body weight, age, sex, and the (genetic) racial background of the patient, activity of the specific compound employed, the metabolic stability and length of action of that compound, the general health, sex, diet, mode and time of administration, rate of excretion, drug combination, and the individual undergoing therapy.

As described above, according to the method of the invention, the compound having formula I as described above is administered to a mammal in need of treatment in a form such that the compound is delivered to the site of action in two or more doses. This is achievable either by the sequential administration of two or more dosage forms of the compound separated by a time interval or by administration of a controlled release preparation which releases the two or more doses at different times.

The amount of each of the two or more doses of a compound of formula (I) as defined above, for example DMXAA or a pharmaceutically acceptable salt or ester thereof required to be effective as an anticancer agent according to the invention will, of course, vary and is ultimately at the discretion of the medical practitioner.

Preferably, the size of each dose is determined with respect to the time interval and the half-life of the compound in the plasma. For example, in one embodiment, if the plasma concentration of the compound e.g. DMXAA which causes toxicity is, say, x micromolar, a first gastrointestinal dose should cause the plasma concentration to reach less than x. After a time interval, a second dose and optionally further doses are given, said second dose (and further doses) being of sufficient magnitude to return the maximum plasma concentration to approximately the original magnitude (e.g. greater than 75%, 85% or 90% of the magnitude attained with the first dose) but still less than x. For example, in a particularly preferred embodiment, wherein the time interval corresponds to approximately one half-life, the second dose may be of approximately half the magnitude of the first dose. This returns the maximum plasma concentration to the original, but it is still less than x. After a further interval of approximately one half-life, a third dose of half the original dose may be given.

As described in the examples, such a regime has been found to be particularly effective for gastrointestinal, e.g. oral, administration in treatment of tumours while avoiding serious toxicity and side effects. The result is particularly surprising because the toxicity associated with the oral use of drugs such as DMXAA was expected to be related to the area under the concentration-time curve (AUC) as with most other drugs and accordingly, it had been expected that the side effects associated with such a regime would have been too serious, rendering the method unacceptable. However, surprisingly, as demonstrated herein, treatment using the dose strategy of the invention is effective without causing unacceptable side effects. Without being limited to any one explanation, it is believed that the results presented herein demonstrate that the toxicity associated with compounds such as DMXAA is related to the maximum concentration and not the AUC as would be expected. This effect is also surprising because effectiveness of i.p. administration is not improved by repeat dosing.

Said first dose may have a magnitude which is equal, greater than or less than one or all of said further doses. Each unit dose may be of equal or different amount from other further doses. In a preferred embodiment, the first dose is greater than the subsequent dose, for example being greater than 1.5 times, for example, greater than about 2, 2.5. 3, 5, 7, or 10 times the magnitude of the subsequent dose or doses. In a particularly preferred embodiment the first dose is approximately twice the size of each subsequent dose. In a particularly preferred embodiment, said first dose is greater than 50%, more preferably greater than 60%, more preferably greater than 70%, more preferably greater than 80%, more preferably greater than 90%, more preferably greater than 95%, more preferably greater than 98% of the maximum tolerated dose when administered as a single oral dose.

In general, a suitable first dose of DMXAA for oral administration to man for treatment of cancer is in the range of 50 to 10000 mg/m$^2$ of DMXAA, and, preferably, 600 to 10000 mg/m$^2$, for example from 600 to 7500 mg/m$^2$ of DMXAA, such as from 600 to 6500 mg/m$^2$ of DMXAA, suitably 1200 to 6500 mg/m$^2$ of DMXAA, particularly 2000 to 6000 mg/m$^2$ of DMXAA, more particularly 3000 to 5500 mg/m$^2$ of DMXAA, more particularly 4000 to 5500 mg/m$^2$ of DMXAA. A particularly preferred dose is in the range 4000 to 5400 mg/m$^2$ of DMXAA. A further particularly preferred dose is in the range 4500 to 5300 mg/m$^2$ of DMXAA. For example, in a preferred embodiment, the first oral dose administered is in the range 5250-5450 mg/m$^2$ of DMXAA with one, preferably two subsequent doses each in the range 2600-2725 mg/m$^2$ of DMXAA. In a particularly preferred embodiment, the first oral dose administered is the maximum tolerated oral dose (MTD) of DMXAA, which is approximately 5300 mg/m$^2$. Other suitable doses may be in the lower range, for example, from 50 to 600 mg/m$^2$.

The time interval between doses (which may be the time interval between sequentially administered separate dosage forms or the time interval between release of separate doses from a controlled release formulation) is generally greater than 1 hour, preferably, greater than 2 hours, more preferably greater than 3 hours. In a preferred embodiment, said doses are separated by a time interval of less than 24 hours, for example, 4 hours, 6 hours or 8 hours. It is to be understood that the present invention covers all combinations of suitable and preferred groups described herein above.

The present invention will now be described only by way of example and with reference to the accompanying figures, wherein:

FIG. 1; Expt. II shows relative tumour volume of colon 38 tumours untreated (circle), or following treatment with DMXAA (30+15+15 mg/kg orally at 4 hour intervals, triangle), DMXAA (30 mg/kg single dose orally, diamond), DMXAA (15+15 mg/kg at 4 hour intervals, triangle). Mean±SEM (standard error of the mean) of 5 mice per group.

EXAMPLES

Experiments 1 and 2

Materials and Methods

C57B1/6 mice from the Animal Resource Unit, University of Auckland, were bred and housed under conditions of constant temperature and humidity, with sterile bedding and food, according to institutional ethical guidelines. All mice were aged between 8 and 12 weeks.

Drugs and Drug Administration

DMXAA was synthesized as the sodium salt (Rewcastle et al (1990) Journal of National Cancer Institute 82:528-529). DMXAA sodium salt was dissolved in sterile water and was administered orally by gavage.

Tumour Growth

Colon 38 tumour fragments (~1 mm$^3$) were implanted subcutaneously (s.c.) in the left flank of anaesthetized (sodium pentobarbital, 81 mg/kg) mice. The experiments were initiated when tumours were approximately 3-4 mm (approximately 20 mg mass) in diameter. Tumour-bearing mice were treated with drugs according to the administration schedule described before, and the tumours measured using calipers, three times weekly thereafter. Tumour volumes were calculated as $0.52a^2b$, where a and b are the minor and major axes of the tumour, respectively. For graphical representation the arithmetic means were calculated for each time point, counting cured tumours as zero volume.

Data Analysis

Experiment I

Two groups of 5 mice were implanted with tumours. The treatment group received DMXAA according to the schedule shown, the control group received no DMXAA. The individual mice in each group were not marked, and so any one line of the spreadsheet data shown in Table 1 could be from any individual mouse of a particular group. Therefore, the spreadsheet does not show which data point is from which animal and, therefore, how much any one tumour has grown relative to its initial size.

Figure 1:
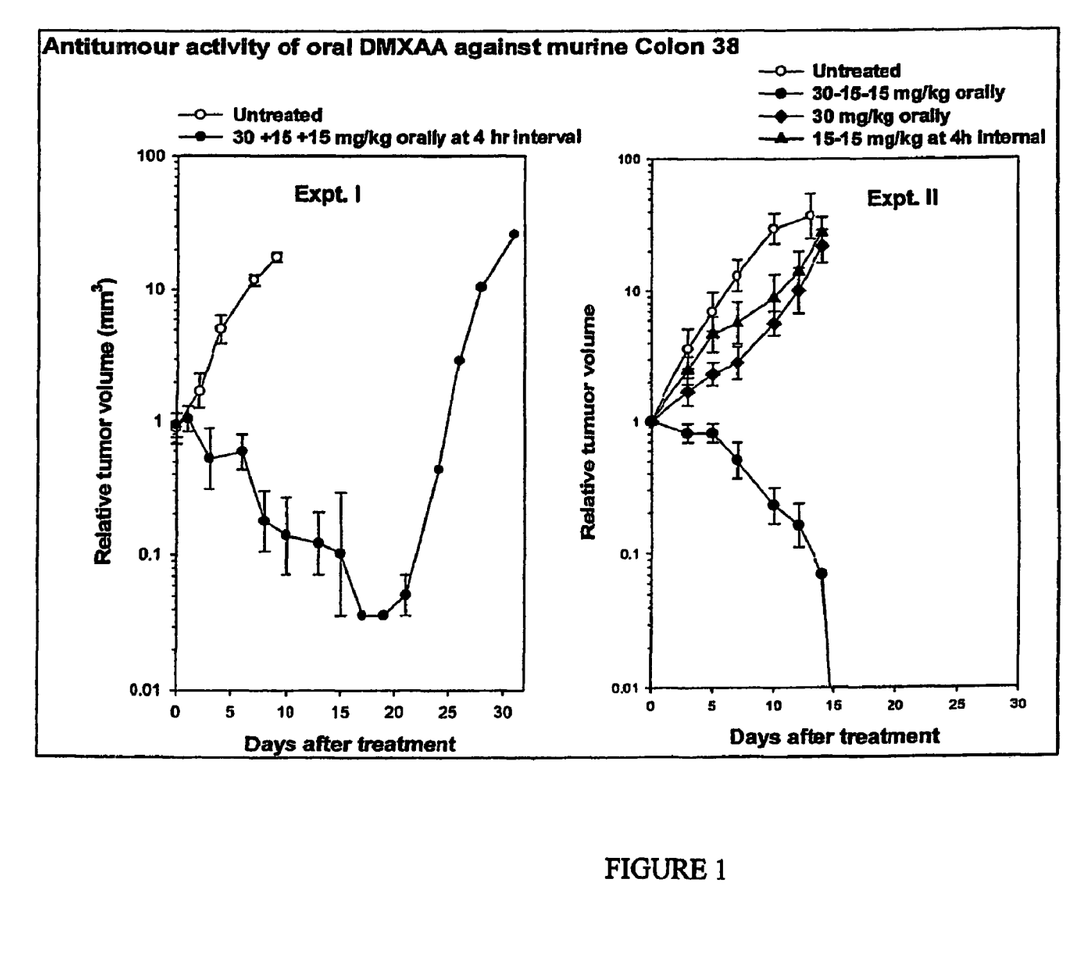
FIG. 1; Expt. I shows relative tumour volume of colon 38 tumours untreated (circle), or following treatment with DMXAA (30+15+15 mg/kg orally at 4 hour intervals, triangle), Mean±SEM (standard error of the mean) of 5 mice per group.
Figure 2:
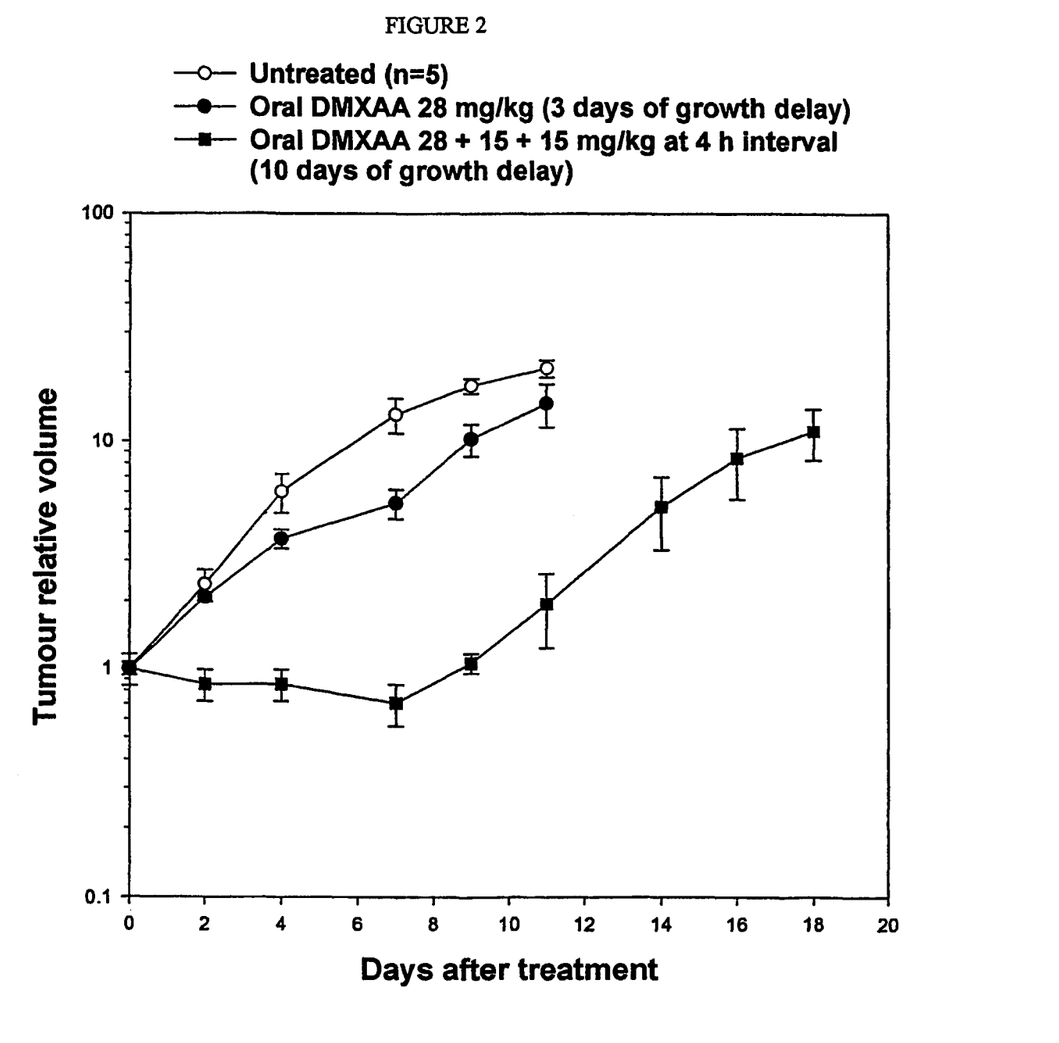
FIG. 2 shows the activity by oral dosing in nude mice bearing a human colon carcinoma xenograft (HT29).

The data were normalised, to enable plotting of the average tumour growth beginning from a relative size of 1 (see FIG. 1). This was done as follows:

all tumour sizes ($a_1, a_2 \ldots a_n$) on the first day were added=x (e.g. gives 78.0 for the untreated mice)

x was divided by the number of mice (n) (e.g. 78.0/5=15.6 for untreated mice)=y

Each individual data point ($a_1, a_2 \ldots a_n$) is divided by y for every day of the experiment (e.g. for first mouse in control group on first day 5.7/15.6=0.365, on second day 23.6/15.6=1.51 etc)

Thus, the total tumour size on the first day is 5, the average is 1, and every subsequent average of the normalised data shows average growth relative to 1.

TABLE 1

Actual tumour sizes for mice treated as described in Experiment I

| Treatment | Tumor volume (mm³)* | | | | |
|---|---|---|---|---|---|
| | 0 day | 1 day | 3 day | 6 day | 8 day |
| Untreated | 5.7 | 23.6 | 31.5 | 251.6 | 235.9 |
| | 12.6 | 23.6 | 130.8 | 178.3 | 235.9 |
| | 12.6 | 39.6 | 84.8 | 140.1 | 266.4 |
| | 23.6 | 10.1 | 77.1 | 165.6 | 285.4 |
| | 23.6 | 61.6 | 110.7 | 204.4 | 362.3 |

| | 0 day | 1 day | 3 day | 6 day | 8 day | 10 day | 13 day | 15 day |
|---|---|---|---|---|---|---|---|---|
| 30 – 15 – 15 | 6.3 | 18.8 | 6.3 | 6.3 | 0.0 | 14.1 | 4.2 | 0.0 |
| mg/kg orally | 18.8 | 18.8 | 18.8 | 0.0 | 1.0 | 1.0 | 0.0 | 0.5 |
| DMXAA | 18.8 | 18.8 | 1.0 | 14.1 | 1.0 | 1.0 | 1.0 | 0.0 |
| | 14.1 | 6.3 | 14.1 | 4.2 | 6.3 | 0.0 | 0.5 | 4.2 |
| | 14.1 | 18.8 | 14.1 | 14.1 | 6.3 | 1.0 | 4.2 | 0.0 |

| | 17 day | 19 day | 21 day | 24 day | 26 day | 28 day | 31 day |
|---|---|---|---|---|---|---|---|
| 30 – 15 – 15 | 0.5 | 0.0. | 0.0 | 0.0 | 0.0 | 150.3 | 373.4 |
| mg/kg orally | 0.0 | 0.0 | 0.0 | 0.0 | 0.0 | 0.0 | 0.0 |
| DMXAA | 0.0 | 0.0 | 0.0 | 0.0 | 0.0 | 0.0 | 0.0 |
| | 0.0 | 0.0 | 0.0 | 0.0 | 0.0 | 0.0 | 0.0 |
| | 0.5 | 0.5 | 1.0 | 6.3 | 41.7 | 0.0 | 0.0 |

*0.52 × (the minor axes)² × major tumour axes

TABLE 2

Normalised data for mice treated as described in Experiment I

| Expt I normalised data | Time (days) | | | | |
|---|---|---|---|---|---|
| Control | 0 | 2 | 4 | 7 | 9 |
| | 0.36 | 1.51 | 2.02 | 16.13 | 15.12 |
| | 0.81 | 1.51 | 8.39 | 11.43 | 15.12 |
| | 0.81 | 2.54 | 5.43 | 8.98 | 17.08 |
| | 1.51 | 0.65 | 4.94 | 10.62 | 18.30 |
| | 1.51 | 3.95 | 7.10 | 13.10 | 23.22 |

| | Time (days) | | | | | | |
|---|---|---|---|---|---|---|---|
| | 0 | 1 | 3 | 6 | 8 | 10 | 13 |
| 30 + 15 + 15 | 0.43 | 1.30 | 0.43 | 0.43 | 0 | 0.98 | 0.29 |
| DMXAA | 1.30 | 1.30 | 1.30 | 0.00 | 0.07 | 0.07 | 0.00 |
| | 1.30 | 1.30 | 0.07 | 0.98 | 0.07 | 0.07 | 0.07 |
| | 0.98 | 0.43 | 0.98 | 0.29 | 0.43 | 0.00 | 0.04 |
| | 0.98 | 1.30 | 0.98 | 0.98 | 0.43 | 0.07 | 0.29 |

TABLE 2-continued

Normalised data for mice treated as described in Experiment I

| | Time (days) | | | | | | | |
|---|---|---|---|---|---|---|---|---|
| | 15 | 17 | 19 | 21 | 24 | 26 | 28 | 31 |
| 30 + 15 + 15 | 0 | 0.04 | 0 | 0 | 0 | 0 | 10.44 | 25.93 |
| DMXAA | 0.04 | 0.00 | 0 | 0 | 0 | 0 | 0 | 0 |
| | 0.00 | 0.00 | 0 | 0 | 0 | 0 | 0 | 0 |
| | 0.29 | 0.00 | 0.04 | 0.04 | 0 | 0 | 0 | 0 |
| | 0 | 0.04 | 0.04 | 0.07 | 0.43 | 2.90 | 0 | 0 |

Experiment II

This example was performed using four groups of mice. Group 1 (control, n=5) received no treatment. Group 2 (n=5) received two 15 mg/kg doses of DMXAA. Group 3 (n=5) received a single 30 mg/kg dose of DMXAA. Group 4 (n=6) received three doses of DMXAA in concentrations of 30+15+ 15 mg/kg. In this experiment tumours were all 14 mm³ at the start of the experiment. Data were normalised by division by 14 to give size relative to initial size.

TABLE 3

Actual tumour sizes for mice treated as described in Experiment II

| Treatment | Tumor volume (mm³)* | | | | |
|---|---|---|---|---|---|
| Untreated | 0 day | 3 day | 5 day | 7 day | 10 day |
| | 14.0 | 140.4 | 299.5 | 442.3 | 442.3 |
| | 14.0 | 78.1 | 126.4 | 140.4 | 299.5 |
| | 14.0 | 31.2 | 50.0 | 97.4 | 191.1 |
| | 14.0 | 52.7 | 93.6 | 263.3 | 898.6 |
| | 14.0 | 18.7 | 50.0 | 130.0 | 547.6 |

TABLE 3-continued

Actual tumour sizes for mice treated as described in Experiment II

|  | 0 day | 3 day | 5 day | 7 day | 10 day | 12 day | 14 day |
|---|---|---|---|---|---|---|---|
| 30 mg/kg orally DMXAA | 14.0 | 14.0 | 17.6 | 17.6 | 50.0 | 55.3 | 140.4 |
|  | 14.0 | 48.7 | 48.7 | 58.5 | 91.0 | 152.9 | 347.5 |
|  | 14.0 | 33.3 | 33.3 | 41.6 | 152.9 | 332.7 | 505.4 |
|  | 14.0 | 23.4 | 50.0 | 91.0 | 91.0 | 332.7 | 623.9 |
|  | 14.0 | 14.0 | 25.0 | 25.0 | 50.0 | 58.5 | 172.0 |

|  | 0 day | 3 day | 5 day | 7 day | 10 day | 12 day | 14 day | 17 day |
|---|---|---|---|---|---|---|---|---|
| 30 – 16 – 15 mg/kg orally DMXAA | 14.0 | 9.4 | 9.4 | 2.4 | 0.0 | 0.0 | 0.0 | 0.0 |
|  | 14.0 | 6.2 | 6.2 | 4.2 | 1.0 | 1.0 | 0.0 | 0.0 |
|  | 14.0 | 10.5 | 10.5 | 4.6 | 3.1 | 0.8 | 0.0 | 0.0 |
|  | 14.0 | 18.7 | 14.0 | 14.0 | 6.2 | 4.2 | 1.0 | 0.0 |
|  | 14.0 | 14.0 | 14.0 | 14.0 | 4.2 | 4.1 | 1.0 | 0.0 |
|  | 14.0 | 14.0 | 18.7 | 14.0 | 4.2 | 4.2 | 1.0 | 0.0 |

|  | 0 day | 3 day | 5 day | 7 day | 10 day | 12 day | 14 day |
|---|---|---|---|---|---|---|---|
| 15 – 15 mg/kg orally DMXAA | 14.0 | 47.3 | 85.9 | 96.7 | 96.7 | 126.4 | 263.3 |
|  | 14.0 | 14.0 | 31.2 | 31.2 | 37.5 | 112.3 | 249.6 |
|  | 14.0 | 31.2 | 31.2 | 37.5 | 78.1 | 112.3 | 249.6 |
|  | 14.0 | 58.5 | 112.3 | 172.0 | 274.6 | 274.6 | 546.0 |
|  | 14.0 | 41.6 | 131.0 | 168.3 | 366.0 | 676.0 | 973.4 |

*0.52 × (the minor axes)$^2$ × major tumour axes

TABLE 4

Normalised data for mice treated as described in Experiment II

| Expt II -normalised data | Time | | | | | |
|---|---|---|---|---|---|---|
| Oral | 0 | 3 | 5 | 7 | 10 | 13 |
| control group Normalised data | 1 | 10 | 21.33 | 31.5 | 31.5 | |
|  | 1 | 5.56 | 9 | 10 | 21.33 | 24.89 |
|  | 1 | 2.22 | 3.56 | 6.94 | 13.61 | 24.89 |
|  | 1 | 3.75 | 6.67 | 18.75 | 64 | 81 |
|  | 1 | 1.33 | 3.56 | 9.26 | 39 | |

|  | 0 | 3 | 5 | 7 | 10 | 12 | 14 | 17 |
|---|---|---|---|---|---|---|---|---|
| DMXAA Oral 30 – 15 – 15 mg/kg | 1 | 0.67 | 0.67 | 0.17 | 0 | 0 | 0 | 0 |
|  | 1 | 0.44 | 0.44 | 0.3 | 0.07 | 0.07 | 0 | 0 |
|  | 1 | 0.75 | 0.75 | 0.33 | 0.22 | 0.06 | 0 | 0 |
|  | 1 | 1.33 | 1 | 1 | 0.44 | 0.3 | 0.07 | 0 |
|  | 1 | 1 | 1 | 1 | 0.3 | 0.29 | 0.07 | 0 |
|  | 1 | 1 | 1.33 | 1 | 0.3 | 0.3 | 0.07 | 0 |

|  | 0 | 3 | 5 | 7 | 10 | 12 | 14 |
|---|---|---|---|---|---|---|---|
| Oral 15 – 15 mg/kg | 1 | 3.37 | 6.12 | 6.89 | 6.89 | 9 | 18.75 |
|  | 1 | 1 | 2.22 | 2.22 | 2.67 | 8 | 17.78 |
|  | 1 | 2.22 | 2.22 | 2.67 | 5.56 | 8 | 17.78 |
|  | 1 | 4.17 | 8 | 12.25 | 19.56 | 19.56 | 38.89 |
|  | 1 | 2.96 | 9.33 | 11.99 | 26.07 | 48.15 | 69.33 |

|  | 0 | 3 | 5 | 7 | 10 | 12 | 14 |
|---|---|---|---|---|---|---|---|
| Oral 30 mg/kg | 1 | 1 | 1.25 | 1.25 | 3.56 | 3.94 | 10 |
|  | 1 | 3.47 | 3.47 | 4.17 | 6.48 | 10.89 | 24.75 |
|  | 1 | 2.37 | 2.37 | 2.96 | 10.89 | 23.7 | 36 |
|  | 1 | 1.67 | 3.58 | 6.48 | 6.48 | 23.7 | 44.44 |
|  | 1 | 1 | 1.78 | 1.78 | 3.56 | 4.17 | 12.25 |

Results

Experiment I

The tumour growth delay experiment was conducted using 2 drug regimes: untreated controls (n=5) and oral DMXAA (n=5) administered in 3 doses. The first dose (30 mg/kg), was administered at t=0 hours followed by two lower doses each of 15 mg/kg at t=4 hours and t=8 hours respectively. Tumour size was measured thrice weekly and the results normalised as described above. The results are shown in Table 1 (raw data), Table 2 (normalised data) and FIG. 1, Expt. I (plotted as a graph).

As shown in FIG. 1, Expt. I, in the control group, tumours continued to grow throughout the time-course of the experiment. In contrast, in the treatment group, average tumour size decreased throughout the first 17 days of the experiment with 4/5 mice cured completely within 24 days. In one animal, after initial tumour size reduction, tumour size began to increase approximately 17 days after treatment.

Experiment II

In this example, the tumour growth delay experiment was conducted using 4 drug regimes: untreated controls (Group 1, n=5); two 15 mg/kg doses of DMXAA separated by a 4 hour interval (Group 2, n=5); a single 30 mg/kg dose of DMXAA (Group 3, n=5); three doses of DMXAA in concentrations of 30+15+15 mg/kg administered at t=0, 4 and 8 hours respectively (Group 4, n=6). The 30 mg/kg dose is the maximum tolerated single dose Zhao et al (Cancer Chemother Pharmacol. 2002 January; 49(1):20-6). Tumour size was measured thrice weekly and the results normalised as described above. The results are shown in Table 3 (raw data), Table 4 (normalised data) and FIG. 1, Expt. II (plotted as a graph).

As shown in FIG. 1, Expt. II, in the control group, the single dose group, the 30 mg/kg dose group and the 2×15 mg/kg dose group, tumours continued to grow throughout the time-course of the experiment. In contrast, in the 30+15+15 mg/kg treatment group, average tumour size decreased throughout the first 17 days of the experiment with 6/6 mice cured completely within 17 days.

Therefore, in contrast to other treatment regimes, in particular a single dose at the maximum tolerated dose (MTD), the multiple dose strategy surprisingly resulted in a very significant anti-tumour effect without the serious side effects which would be expected given the area under the concentration curve.

Experiment 3

Methods

Nude mice were implanted with 5×10⁶ HT29 human colon cancer cells, subcutaneously. When tumours had reached a diameter of 6-8 mm, mice were randomised into groups of 5 and received either no drug (untreated controls), DMXAA (sodium salt) at a single oral dose of 28 mg/kg or DMXAA (sodium salt) at oral doses of 28 mg/kg followed by two additional doses of 15 mg/kg 4 and 8 hours after the initial dose. Tumours were then measured using callipers every 2-3 days and volumes calculated. Comparative tumour growth curves are plotted with respect to those at the onset of treatment (relative tumour volume).

CONCLUSION

DMXAA induces antitumour activity by the oral route against a human colon carcinoma xenograft. Maximum activity was achieved by a schedule involving an initial close maximum tolerated "loading" dose followed by two 50% of initial dose "maintenance" doses.

All publications mentioned in the above specification are herein incorporated by reference. Various modifications and variations of the described methods uses and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A method for treating colon cancer, which comprises orally administering to a mammal, in need of treatment an effective amount of 5,6-dimethylxanthenone-4-acetic acid (DMXAA) or a pharmaceutically acceptable salt or ester thereof;
wherein:
   (i) DMXAA, or a pharmaceutically acceptable salt or ester thereof, is administered in two or more discrete doses, separated by a time interval;
   (ii) the first dose is greater than 50% of a maximum tolerated dose;
   (iii) the first dose is greater than 1.5 times the magnitude of one or more subsequent doses; and
   (iv) said time interval is in a range of 1 to 6 hours, and wherein the maximum tolerated dose of DMXAA is 5300 mg/m².

2. The method according to claim 1 wherein said DMXAA or a pharmaceutically acceptable salt or ester thereof is administered in at least one controlled release formulation.

3. The method according to claim 2 wherein said controlled release formulation is formulated such that, in use, said formulation releases at least two discrete doses of said DMXAA or a pharmaceutically acceptable salt or ester thereof separated by a time interval, wherein the time interval is in the range of 1 to 6 hours.

4. The method according to claim 1 or claim 2 wherein said time interval is 6 hours.

5. The method according to claim 1 wherein the first dose is in the range of 3000 to 5300 mg/m².

6. The method according to claim 1 wherein the first dose is in the range of 4000 to 5300 mg/m².

7. The method of claim 6 wherein two subsequent doses are in the range of 2600 to 2725 mg/m².

8. The method of claim 1 wherein a subsequent dose is in the range of 2600 to 2725 mg/m².

9. The method according to claim 1, wherein said mammal is a human.

* * * * *

UNITED STATES PATENT AND TRADEMARK OFFICE
CERTIFICATE OF CORRECTION

PATENT NO. : 7,585,893 B2 Page 1 of 1
APPLICATION NO. : 11/116798
DATED : September 8, 2009
INVENTOR(S) : Baguley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 144 days.

Signed and Sealed this

Fourteenth Day of September, 2010

David J. Kappos
*Director of the United States Patent and Trademark Office*